(12) United States Patent
Jennings et al.

(10) Patent No.: US 7,259,182 B2
(45) Date of Patent: Aug. 21, 2007

(54) ARYL, ARYLOXY, AND AKLYLOXY SUBSTITUTED 1H-INDOL-3-YL GLYOXYLIC ACID DERIVATIVES AS INHIBITORS OF PLASMINOGEN ACTIVATOR INHIBITOR-1 (PAI-1)

(75) Inventors: Lee Dalton Jennings, Chestnut Ridge, NJ (US); Hassan Mahmoud Elokdah, Yardley, PA (US); Geraldine Ruth McFarlane, Monmouth Junction, NJ (US)

(73) Assignee: Wyeth, Madison, NJ (US)

( * ) Notice: Subject to any disclaimer, the term of this patent is extended or adjusted under 35 U.S.C. 154(b) by 428 days.

(21) Appl. No.: 10/731,308

(22) Filed: Dec. 9, 2003

(65) Prior Publication Data
US 2004/0138283 A1 Jul. 15, 2004

Related U.S. Application Data

(60) Provisional application No. 60/432,329, filed on Dec. 10, 2002.

(51) Int. Cl.
A61K 31/404 (2006.01)
C07D 209/04 (2006.01)

(52) U.S. Cl. ............ 514/419; 548/469; 548/490; 548/491; 548/127; 514/415; 546/268.1; 546/277.4

(58) Field of Classification Search ........... 548/469, 548/490, 491, 127; 514/415, 419; 546/268.1, 546/277.4
See application file for complete search history.

(56) References Cited

U.S. PATENT DOCUMENTS

| | | | | |
|---|---|---|---|---|
| 3,026,325 A | 3/1962 | Heinzelman et al. | | 548/496 |
| 3,476,770 A | 11/1969 | Scherrer | | 548/494 |
| 3,557,142 A | 1/1971 | Bell | | 548/516 |
| 3,843,683 A | 10/1974 | Bell | | 548/493 |
| 4,478,819 A | 10/1984 | Hercelin et al. | | 424/457 |
| 4,736,043 A | 4/1988 | Michel et al. | | 548/492 |
| 4,851,406 A | 7/1989 | Martens et al. | | 514/217.04 |
| 5,164,372 A | 11/1992 | Matsuo et al. | | 514/19 |
| 5,420,289 A | 5/1995 | Musser et al. | | 548/159 |
| 5,482,960 A | 1/1996 | Berryman | | 514/414 |
| 5,502,187 A | 3/1996 | Ayer et al. | | 544/117 |
| 5,541,343 A | 7/1996 | Himmelsbach et al. | | 544/424 |
| 5,612,360 A | 3/1997 | Boyd et al. | | 514/381 |
| 5,859,044 A | 1/1999 | Dow et al. | | 514/419 |
| 6,048,875 A | 4/2000 | De Nanteuil et al. | | 514/314 |
| 6,110,963 A | 8/2000 | Malamas | | 514/443 |
| 6,166,069 A | 12/2000 | Malamas et al. | | 514/469 |
| 6,232,322 B1 | 5/2001 | Malamas et al. | | 514/303 |
| 6,251,936 B1 | 6/2001 | Wrobel et al. | | 514/443 |
| 6,302,837 B1 | 10/2001 | De Nanteuil et al. | | 514/337 |
| 6,479,524 B1 | 11/2002 | Priepke et al. | | 514/352 |
| 6,599,929 B2 | 7/2003 | Cho et al. | | 514/415 |
| 6,787,556 B1 | 9/2004 | Hargreaves et al. | | 514/311 |
| 6,800,645 B1 | 10/2004 | Cox et al. | | 514/314 |
| 6,800,654 B2 | 10/2004 | Mayer et al. | | 514/381 |
| 6,844,358 B2 | 1/2005 | Malamas et al. | | 514/336 |
| 2003/0013732 A1 | 1/2003 | Elokdah | | 514/301 |
| 2003/0018067 A1 | 1/2003 | Elokdah et al. | | 514/469 |
| 2003/0060497 A1 | 3/2003 | Gerlach | | 514/414 |
| 2003/0125371 A1 | 7/2003 | Elokdah et al. | | 514/419 |
| 2004/0116488 A1 | 6/2004 | Jennings et al. | | 514/374 |
| 2004/0116504 A1 | 6/2004 | Elokdah et al. | | 514/419 |
| 2004/0122070 A1 | 6/2004 | Jennings | | 514/374 |
| 2004/0204417 A1 | 10/2004 | Perez et al. | | 514/249 |
| 2005/0070584 A1 | 3/2005 | Havran et al. | | 514/357 |
| 2005/0070585 A1 | 3/2005 | Elokdah et al. | | 514/364 |
| 2005/0070587 A1 | 3/2005 | Elokdah et al. | | 514/381 |
| 2005/0070592 A1 | 3/2005 | Gundersen | | 514/415 |
| 2005/0096377 A1 | 5/2005 | Hu | | 514/419 |
| 2005/0113428 A1 | 5/2005 | Gopalsamy et al. | | 514/364 |
| 2005/0113439 A1 | 5/2005 | Hu | | 514/414 |
| 2005/0119296 A1 | 6/2005 | Elokdah et al. | | 514/300 |
| 2005/0119326 A1 | 6/2005 | Havran et al. | | 514/414 |
| 2005/0119327 A1 | 6/2005 | Hu | | 514/414 |
| 2005/0215626 A1 | 9/2005 | Havran et al. | | 514/469 |

(Continued)

FOREIGN PATENT DOCUMENTS

DE 3147276 A1 6/1983

(Continued)

OTHER PUBLICATIONS

U.S. Appl. No. 10/947,710, filed Sep. 23, 2004, Commons et al.

(Continued)

Primary Examiner—Golam M. M. Shameem
(74) Attorney, Agent, or Firm—Woodcock Washburn LLP

(57) ABSTRACT

Compounds of formula I are provided:

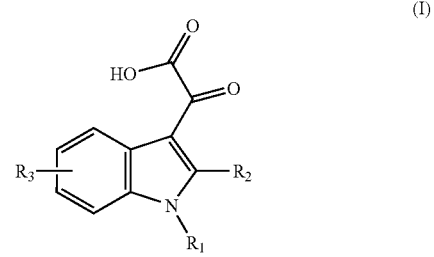

(I)

wherein:

R1, R2, and R3, are as defined herein, as well as pharmaceutical composition and methods using the compounds as inhibitors of plasminogen activator inhibitor (PAI-1) and as therapeutic composition for treating conditions resulting from fibrinolytic disorders, such as deep vein thrombosis, coronary heart disease and pulmonary fibrosis.

40 Claims, No Drawings

U.S. PATENT DOCUMENTS

| | | | |
|---|---|---|---|
| 2005/0113436 A1 | 5/2005 | Elokdah et al. ............. | 514/411 |
| 2005/0113437 A1 | 5/2005 | Hu et al. ................... | 514/414 |

FOREIGN PATENT DOCUMENTS

| | | |
|---|---|---|
| DE | 43 38 770 A1 | 5/1995 |
| DE | 19543639 A1 | 5/1997 |
| DE | 19753522 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 | 5/1995 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 | 4/2001 |
| EP | 1 156 045 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | WO96/32379 | 10/1996 |
| WO | 97/09308 A1 | 3/1997 |
| WO | 97/43260 A1 | 11/1997 |
| WO | WO97/48697 | 12/1997 |
| WO | 98/08818 A1 | 3/1998 |
| WO | 99/28297 A1 | 6/1999 |
| WO | 99/43672 A1 | 9/1999 |
| WO | WO99/43651 | 9/1999 |
| WO | WO99/43654 | 9/1999 |
| WO | WO99/46260 | 9/1999 |
| WO | 99/50268 A1 | 10/1999 |
| WO | 99/58519 A1 | 11/1999 |
| WO | 99/61435 A1 | 12/1999 |
| WO | 00/32180 A2 | 6/2000 |
| WO | 00/35919 A1 | 6/2000 |
| WO | 00/46195 A1 | 8/2000 |
| WO | 00/046197 A1 | 8/2000 |
| WO | 00/64876 A1 | 11/2000 |
| WO | 00/64888 A1 | 11/2000 |
| WO | 01/12187 A2 | 2/2001 |
| WO | 02/030895 A1 | 4/2002 |
| WO | 02/072549 A1 | 9/2002 |
| WO | WO 03/000253 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

U.S. Appl. No. 10/947,711, filed Sep. 23, 2004, Gopalsamy et al.

U.S. Appl. No. 11/208,777, filed Aug. 22, 2005, Commons et al.

U.S. Appl. No. 11/208,772, filed Aug. 22, 2005, Commons.

U.S. Appl. No. 11/208,775, filed Aug. 22, 2005, Commons et al.

Aggarwal et al., "A catalytic antibody programmed for torsional activation of amide bond hydrolysis," *Chem. Eur. J.*, Jan. 25, 2003, 9(13), 3132-3142.

Ballantine, J. A., "The Chemistry of Bacteria," *Journal of the Chemical Society Abstracts*, 1957, 2222-2227.

Delgado et al., Journal of Organic Chemistry (1993), 58(10), pp. 2862-2866.

Dillard R. D. et al., "Indole Inhibitors of Human Nonpancreatic Secretory Phospholipase $A_2$ I. Indole-3-Acetamides", *Journal of Medicinal Chemistry*, American Chemical Society, 39(26), 5119-5136.

Hipskind, P. A. et al., "Potent and selective 1,2,3-trisubstituted indole NPY Y-1 antagonists," *J Med Chem*, 1997, 40(23), 3712-3714.

Julia et al., CA 57:49169, 1962.

Malamas, M. S. et al., "Antihyperglycemic activity of new 1,2,4-oxadiazolidine-3,5-diones," *Eur. J. Med. Chem.*, 2001, 36, 31-42.

Malamas, M.S. et al. "Novel benzofuran and benzothiophene biphenyls as inhibitors of protein tyrosine phosphatase 1B with antihyperglycemic properties," *Journal of Medicinal Chemistry*, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," *Zhurnal Organicheskoi Khimii*, 1986, 22(9), 1868-1873.

Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2: 1422-1428.

Guzzo, P.R. et al., "Synthesis of a conformationally constrained threonin-valine dipeptide mimetic: design of a potential inhibitor of plasminogen activator inhibitor-1," Tetrahedron Letters, *Tetrahedron Letters*, 43(1), 41-43 (2002).

Charlton, Peter, "The status of plasminogen activator inhibitor-1 as a therapeutic target," Expert *Opinion On Investigational Drugs*, (May 1997), vol. 6, No. 5, pp. 539-554.

Malamas, M.S. et al. "Characterization and comparative evaluation of a structurally unique PAI-1 inhibitor exhibiting oral in-vivo efficacy," *Journal of Medicinal Chemistry*, 43(7):1293-1310.

Da Settimo, A. et al., "Reaction of indole derivatives with bromine, substitution, oxidation, and dimerization," *J Org Chem*, 1970, 35(8):2546-2551.

Chitra Krishnamurti et al., Blood, Mar. 1987, 798-803, 69(3).

Christopher F. Reilly et al., Arteriosclerosis and Thrombosis, Sep./Oct. 1991, 1276-1286, 11(5).

Peter Carmeliet et al., J. Clin. Investigations, 1993, 2756-2760, 92.

E. Rocha et al., Fibrinolysis, 1994, 294-303, 8.

Justo Aznar et al., Haemostasis, 1994, 243-251, 24.

B.J. Biemond et al., Circulation, 1995, 1175-1181, 91(4).

Marcel Levi et al., Circulation, Jan. 1992, 305-312, 85(1).

Thomas K. Nordt et al., J. Clin. Endocrinology and Metabolism, 2000, 1563-1568, 85(4).

E. Daci et al., J. Bone and Mineral Research, 2000, 1510-1516, 15(8).

ARYL, ARYLOXY, AND AKLYLOXY SUBSTITUTED 1H-INDOL-3-YL GLYOXYLIC ACID DERIVATIVES AS INHIBITORS OF PLASMINOGEN ACTIVATOR INHIBITOR-1 (PAI-1)

This application claims priority from provisional application Ser. No. 60/432,329 filed on Dec. 10, 2002, the entire disclosure of which is hereby incorporated by reference.

This invention relates to aryl, aryloxy, and alkyloxy substituted indol-3-yl glyoxylic acid derivatives which are useful as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (tPA) and urokinase type plasminogen activator (uPA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary fibrosis, Alzheimer's disease, polycystic ovary syndrome, etc.

WO 99/43654 and WO 99/43651 disclose indole derivatives of formula I as inhibitors phospholipase enzymes useful in preventing inflammatory conditions.

(I)

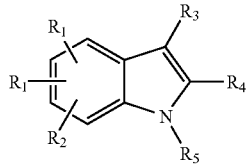

WO 96/32379 discloses PDE-inhibitor compounds of formula I (I)

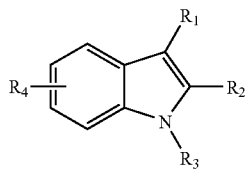

where: $R_1$ is a hydrogen, halogen, nitro, carboxy, protected carboxy, acyl, cyano, hydroxyimino, lower alkenyl, optionally substituted with oxo, or lower alkyl, optionally substituted with protected carboxy, carboxy, or hydrogen, $R_2$ is a hydrogen, halogen, carboxy, lower alkenyl, or acyl or lower alkyl optionally substituted with protected carboxy, carboxy, lower alkoxy or hydroxy, $R_3$ is a lower alkenyl, or lower alkenyl, both optionally substituted with one or more substituents from the group consisting of oxo, aryl, and a heterocyclic group, and $R_4$ is carboxy, protected carboxy, or acyl, cyano, halogen, a heterocyclic group, amino, or lower alkyl EP 0 655 439 relates to 5,6 fused ring bicyclic compounds corresponding formula I as platelet aggregation inhibitors.

(I)

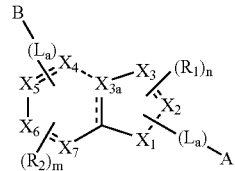

This patent describes 5,6-fused bicyclic ring compounds having both an acidic group "A" linked to the five membered ring by a linking group and a basic group "B" linked to the six membered ring by a linking group.

WO 9748697 relates to substituted azabicyclic compounds including indoles, 2,3-dihydro-1H-indoles, and benzimidazoles of formula (I) for the treatment of conditions ameliorated by the administration of an inhibitor of tumor necrosis factor.

(I)

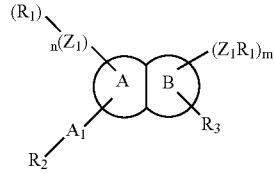

wherein:
A is a five-membered aza heterocycle;
B is a six membered aza heterocycle or an optionally substituted benzene ring;
Z is a bond, O, S, NH;
$A_1$ is a bond, $C_1$–$C_6$ alkyl, $C_2$–$C_6$ alkenyl, or $C_2$–$C_6$ alkynyl;
$R_1$ is hydrogen or $C_1$–$C_4$ alkyl optionally substituted with OH or one or more halo; and
$R_3$ is carboxamide, acyl, substituted alkenyl, substituted alkyl, acylamino, oximino, alkynyl, ketomethyl, aminoalkyl, sulfonylmethyl, sulfinylmethyl, $CF_2OR$, alkylamino, alkoxy, alkylsulfanyl, sulfinyl, acyloxy, sulfonyl, $OCF_2R$, azo, aminosulfonyl, sulfonylamino or aminooxalyl DE 4338770 relates to indole carboxylic acid or tetrazole derivatives of formula (I) useful as phospholipase A2 inhibitors.

(I)

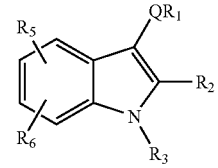

wherein:
Q is CO, $CH_2$, or CHNHCOR,
$R_1$ is XH, Ar, or XAr;
X, Y, Z is 1–19C alkyl, 2–19C alkenyl, 2–19C alkynyl optionally substituted by an O atom;
$R_2$ is COOH, YCOOH, tetrazolyl, or Y-tetrazolyl; and
$R_3$ is H, ZH, Ar, ZAr, ZOR, ZSR, ZNHR

SUMMARY OF THE INVENTION

This invention relates to compounds of the formula I:

(I)

wherein:
$R_1$ is: a) the moiety:

or
b) $C_1$–$C_8$ alkyl, benzo[1,3]dioxo-5ylmethyl, cycloalkylalkyl where the alkyl chain is $C_1$–$C_3$ heteroarylalkyl where the alkyl chain is $C_1$–$C_3$, arylalkyl where the alkyl chain is $C_1$–$C_3$, preferably selected from benzyl, $CH_2$-1-naphthyl, $CH_2$-2-naphthyl, $CH_2CH_2$-phenyl, or $CH_2CH_2$-naphthyl, wherein the alkyl, cycloalkyl, heteroaryl, phenyl, benzyl, and napthyl, groups may be optionally substituted by from 1 to 3 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —C(O)$CH_3$, —$CO_2R_7$, —C(O)$NH_2$, —S(O)$_2$—$CH_3$, —OH, —$NH_2$, or —$NO_2$;
$R_4$ is hydrogen, halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —COOH, —$CH_2CO_2H$, —C(O)$CH_3$, —$CO_2R_7$, —C(O)$NH_2$, —S(O)$_2CH_3$, —OH, —$NH_2$, or —$NO_2$;
X is O, S, or NH;
$R_5$ is $C_1$–$C_8$ alkyl, $C_1$–$C_3$ perfluoroalkyl, $C_3$–$C_6$ cycloalkyl, —$CH_2$—$C_3$–$C_6$ cycloalkyl, heteroaryl, —$CH_2$-heteroaryl, phenyl, or arylalkyl where the alkyl chain is $C_1$–$C_8$, wherein the rings of the cycloalkyl, heteroaryl, phenyl, and aryl groups may be optionally substituted by from 1 to 5 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —COOH, —$CH_2CO_2H$, —C(O)$CH_3$, —$CO_2R_7$, —C(O)$NH_2$, —S(O)$_2CH_3$, —OH, —$NH_2$, or —$NO_2$;
$R_2$ is hydrogen, $C_1$–$C_6$ alkyl, —$CH_2$—$C_3$–$C_6$ cycloalkyl, or $C_1$–$C_3$ perfluoroalkyl, wherein the alkyl and cycloalkyl groups may be optionally substituted by halogen, —CN, $C_1$–$C_6$ alkoxy, —COOH, —$CH_2CO_2H$, —C(O)$CH_3$, —$CO_2R_7$, —C(O)$NH_2$, —S(O)$_2CH_3$, —OH, —$NH_2$, or —$NO_2$;
$R_3$ is: (a) hydrogen, halogen, $C_1$–$C_8$ alkyl, $C_1$–$C_8$ alkenyl, $C_1$–$C_8$ alkynyl, $C_3$–$C_6$ cycloalkyl, —$CH_2$—$C_3$–$C_6$ cycloalkyl, heteroaryl, or phenyl, wherein the alkyl, alkenyl, alkynyl, cycloalkyl, heteroaryl, and phenyl groups may be optionally substituted by from 1 to 3 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —COOH, —$CH_2CO_2H$, —C(O)$CH_3$, —$CO_2R_7$, —C(O)$NH_2$, —S(O)$_2CH_3$, —OH, —$NH_2$, or —$NO_2$;
or (b) the moiety X—$R_6$;
$R_6$ is $C_1$–$C_8$ alkyl, $C_1$–$C_8$ alkenyl, $C_1$–$C_8$ alkynyl, $C_3$–$C_6$ cycloalkyl, —$CH_2$—$C_3$–$C_6$ cycloalkyl, heteroaryl, phenyl, aryl-alkyl where the alkyl chain is $C_1$–$C_8$, $CH_2CH_2$-phenyl, or $CH_2CH_2$-napthyl, wherein the alkyl, alkenyl, alkynyl, cycloalkyl, heteroaryl, phenyl, and napthyl groups may be optionally substituted by from 1 to 3 groups selected from halogen, $C_1$–$C_3$ alkyl, $C_1$–$C_3$ perfluoroalkyl, preferably —$CF_3$, —O—$C_1$–$C_3$ perfluoroalkyl, preferably —$OCF_3$, —S—$C_1$–$C_3$ perfluoroalkyl, preferably —$SCF_3$, $C_1$–$C_3$ alkoxy, —$OCHF_2$, —CN, —C(O)$CH_3$, —$CO_2R_7$, —S(O)$_2$$CH_3$, —OH, —$NH_2$, or —$NO_2$; and
$R_7$ is $C_1$–$C_6$ alkyl, $C_3$–$C_6$ cycloalkyl, —$CH_2$—$C_3$–$C_6$ cycloalkyl, or aryl-alkyl where the alkyl chain is $C_1$–$C_8$;
or a pharmaceutically acceptable salt or ester form thereof.

Preferred compounds of this invention are those of formulas (II) and (III):

(II)

(III)

wherein:
$R_1$ is $C_1$–$C_8$ alkyl, benzo[1,3]dioxo-5yl-methyl, cycloalkylalkyl where the alkyl chain is $C_1$–$C_3$ heteroarylalkyl where the alkyl chain is $C_1$–$C_3$, arylalkyl where the alkyl chain is $C_1$–$C_3$ preferably selected from benzyl, $CH_2$-1-naphthyl, $CH_2$-2-naphyl, CH—$_2CH_2$-phenyl, or $CH_2CH_2$-naphthyl, wherein the alkyl, cycloalkyl, heteroaryl, and aryl groups may be optionally substituted by from 1 to 3 groups selected from halogen, $C_1$–$C_3$ alkyl, $C_1$–$C_3$ perfluoroalkyl, —O—$C_1$–$C_3$ perfluoroalkyl, —S—$C_1$–$C_3$ perfluoroalkyl, $C_1$–$C_3$ alkoxy, —OCHF$_2$, —CN, —COOH, —CH$_2$CO$_2$H, —C(O)CH$_3$, —CO$_2$R$_7$, —C(O)NH$_2$, —S(O)—$_2$CH$_3$, —OH, —NH$_2$, or —NO$_2$;

R$_4$ is hydrogen, halogen, $C_1$–$C_6$ alkyl, $C_1$–$C_3$ haloalkyl, $C_1$–$C_3$ perfluoroalkyl, —O—$C_1$–$C_3$ perfluoroalkyl, —S—$C_1$–$C_3$ perfluoroalkyl, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$;

R$_5$ is $C_1$–$C_8$ alkyl, $C_1$–$C_3$ perfluoroalkyl, —CH$_2$—$C_3$–$C_6$ cycloalkyl, —CH$_2$-heteroaryl, or aryl-alkyl where the alkyl chain is $C_1$–$C_3$, wherein the rings of the cycloalkyl, heteroaryl, and aryl groups may be optionally substituted by from 1 to 5 groups selected from halogen, $C_1$–$C_3$ alkyl, $C_1$–$C_3$ perfluoroalkyl, —O—$C_1$–$C_3$ perfluoroalkyl, —S—C1–C3 perfluoroalkyl, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$;

R$_2$ is hydrogen, $C_1$–$C_6$ alkyl, or $C_1$–$C_3$ perfluoroalkyl, wherein the alkyl group may be optionally substituted by halogen, —CN, $C_1$–$C_6$ alkoxy, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;

R$_3$ is hydrogen, halogen, $C_1$–$C_8$ alkyl, $C_1$–$C_8$ alkenyl, $C_1$–$C_8$ alkynyl, $C_3$–$C_6$ cycloalkyl, —CH$_2$—$C_3$–$C_6$ cycloalkyl, heteroaryl, or phenyl, wherein the alkyl, alkenyl, alkynyl, cycloalkyl, heteroaryl, and phenyl groups may be optionally substituted by from 1 to 3 groups selected from halogen, $C_1$–$C_3$ alkyl, $C_1$–$C_3$ perfluoroalkyl, preferably —CF$_3$, —O—$C_1$–$C_3$ perfluoroalkyl, preferably —OCF$_3$, —S—$C_1$–$C_3$ perfluoroalkyl, preferably —SCF$_3$, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$;

R$_6$ is $C_1$–$C_8$ alkyl, $C_1$–$C_8$ alkenyl, $C_1$–$C_8$ alkynyl, $C_3$–$C_6$ cycloalkyl, —CH$_2$—$C_3$–$C_6$ cycloalkyl, heteroaryl, phenyl, aryl-alkyl where the alkyl chain is $C_1$–$C_8$, CH$_2$CH$_2$-phenyl, or CH$_2$CH$_2$-naphthyl, wherein the alkyl, alkenyl, alkynyl, cycloalkyl, heteroaryl, phenyl, and naphthyl groups may be optionally substituted by from 1 to 3 groups selected from halogen, $C_1$–$C_3$ alkyl, $C_1$–$C_3$ perfluoroalkyl, preferably —CF$_3$, —O—$C_1$–$C_3$ perfluoroalkyl, preferably —OCF$_3$, —S—$C_1$–$C_3$ perfluoroalkyl, preferably —SCF$_3$, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$; and R$_7$ is $C_1$–$C_6$ alkyl, $C_3$–$C_6$ cycloalkyl, —CH$_2$—$C_3$–$C_6$ cycloalkyl, or $C_1$–$C_8$ aryl-alkyl where the alkyl chain is $C_1$–$C_8$;

or a pharmaceutically acceptable salt or ester form thereof.

Specific examples of compounds according to this invention include:

(1-{4-[(4-Cyanobenzyl)oxy]phenyl}-1-H-indol-3-yl)(oxo)acetic acid;

{1-{4-(3-Methoxybenzyloxy)-phenyl}1H-indol-3-yl}-oxo-acetic acid;

{1-(4-(3-Chlorobenzyloxy)-phenyl]1-H-indol-3-yl}-oxo acetic acid;

{1-{4-(4-Cyanobenzyloxy)-phenyl]-5-fluoro-1H-indol-3-yl}-oxo acetic acid;

{1-{4-(3,5-Dimethoxybenzyloxy)-phenyl]-5-fluoro-1H-indol-3-yl}-oxo acetic acid;

{1-[4-(3-Chlorobenzyloxy)-phenyl]-5-methyl-1H-indol-3yl}-oxo acetic acid;

{1-[4-(4-tert Butylbenzyloxy)-phenyl]-5-methyl-1H-indol-3-yl}-oxo acetic acid;

{1-[4-(2,4-Dichlorobenzyloxy)-phenyl]-5-methyl-1H-indol-3yl}-oxo acetic acid;

{5-Chloro-1-[3-(4-cyanobenzyloxy)-phenyl]-1H-indol-3yl}-oxo acetic acid;

{5-Chloro-1-[3-(3,5-dimethoxybenzyloxy)-phenyl]-1H-indol-3yl}-oxo acetic acid;

{1-[4-(2,3,5,6-tetrafluoro-4-trifluoromethylbenzyloxy)-phenyl]1H-indol-3yl]-oxo acetic acid;

{1-[4-(4-[1,2,3]thiadiazol-4-yl benzyloxy)-phenyl]-1H indol-3yl}-oxo acetic acid;

{1-[4-(2,6,-Dichloropyridin-4-yl methoxy)-phenyl]1H-indol-3yl}-oxo acetic acid;

5-[4-(5-Fluoro-3-carboxy(oxo)methyl-1H-indol-1-yl)phenoxymethyl]-furan-2 carboxylic acid ethyl ester;

{1-[4-(2,6,-Dichloropyridin-4-yl methoxy)-phenyl]-5-methyl-1H-indol-3yl}-oxo acetic acid;

{5-Chloro-1-[3-(2,3,5,6-tetrafluoro-4-trifluromethyl-benzyloxy)-phenyl]-1H-indol-3-yl}-oxo acetic acid;

5-[3-(5-Chloro-3-carboxy(oxo)methyl-1H-indol-1-yl)phenoxy methyl]furan-2-carboxylic acid ethyl ester;

{5-Chloro-1-[3-(4-[1,2,3]thiadiazol-4-yl benzyloxy)-phenyl]-1H indol-3yl}-oxo acetic acid;

{5-Chloro-1-[3-(2,6-dichloropyridin-4-yl methoxy)-phenyl]1H-indol-3yl}-oxo acetic acid;

[1,5-Bis-(4-trifluoromethoxy-phenyl)-1H-indol-3-yl]-oxo-acetic acid;

{1-(4-Fluorobenzyl)-5-{2-(4-fluorophenyl)ethoxy}-1H-indol-3-yl}(oxo)acetic acid;

(1-Benzyl-5-benzyloxy-1H-indol-3-yl)-oxo-acetic acid;

{1-Benzyl-5-(2-chloro-4-trifluoromethylphenoxy)-1H-indol-3yl](oxo)acetic acid;

(5-Allyloxy-1-cyclobutylmethyl-1H-indol-3-yl)-oxo-acetic acid;

(5-Allyloxy-1-phenethyl-1H-indol-3-yl)-oxo-acetic acid;

(5-Allyloxy-1-benzo[1,3]dioxol-5-ylmethyl-1H-indol-3-yl)-oxo-acetic acid;

{5-Allyloxy-1-[2-(4-methoxyphenyl)-ethyl]-1H-indol-3-yl}-oxo-acetic acid;

[5-Allyloxy-1-(2-naphthalen-1-yl-ethyl)-1H-indol-3-yl]-oxo-acetic acid;

{5-Allyloxy-1-[2-(3-trifluoromethylphenyl)-ethyl]-1H-indol-3-yl}-oxo-acetic acid;

{5-Allyloxy-1-[2-(4-bromophenyl)-ethyl]-1H-indol-3-yl}-oxo-acetic acid;

or pharmaceutically acceptable salt or ester forms thereof.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylamine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkyl diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hyroxyethyl)-piperidine, or pyridine. Quaternary salts may also be formed, such as tetraalkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —COOR$_9$ wherein R$_9$ is selected from the formulae:

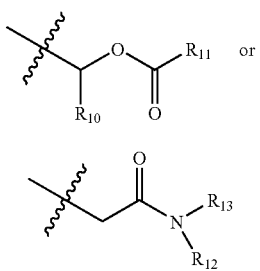

wherein R$_{10}$, R$_{11}$, R$_{12}$, and R$_{13}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$–$C_6$ alkyl esters, $C_3$–$C_6$ branched alkyl esters, benzyl esters, etc.

For purposes of this invention the term "alkyl" includes both straight and branched alkyl moieties, preferably of 1 to 8 carbon atoms. The term "alkenyl" refers to a radical aliphatic hydrocarbon containing one double bond and includes both straight and branched alkenyl moieties of 2 to 7 carbon atoms. Such alkenyl moieties may exist in the E or Z configurations; the compounds of this invention include both configurations. The term "alkynyl" includes both straight chain and branched moieties containing 2 to 7 carbon atoms having at least one triple bond. The term "cycloalkyl" refers to alicyclic hydrocarbon groups having 3 to 12 carbon atoms and includes but is not limited to: cyclopropyl, cyclobutyl, cyclopentyl, cyclohexyl, cycloheptyl, norbornyl, or adamantyl. For purposes of this invention the term "aryl" is defined as an aromatic hydrocarbon moiety and may be substituted or unsubstituted. An aryl may be selected from but not limited to, the group: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups.

For purposes of this invention the term "heteroaryl" is defined as an aromatic heterocyclic ring system (monocyclic or bicyclic) where the heteroaryl moieties are five or six membered rings containing 1 to 4 heteroatoms selected from the group consisting of S, N, and O, and include but is not limited to: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, pyrrolidinyl; (2) a bicyclic aromatic heterocycle where a phenyl, pyridine, pyrimidine or pyridazine ring is: (i) fused to a 6-membered aromatic (unsaturated) heterocyclic ring having one nitrogen atom; (ii) fused to a 5 or 6-membered aromatic (unsaturated) heterocyclic ring having two nitrogen atoms; (iii) fused to a 5-membered aromatic (unsaturated) heterocyclic ring having one nitrogen atom together with either one oxygen or one sulfur atom; or (iv) fused to a 5-membered aromatic (unsaturated) heterocyclic ring having one heteroatom selected from O, N or S.

For the purposes of this invention the term "alkoxy" is defined as $C_1$–$C_6$ alkyl-O—; wherein alkyl is defined above.

For purposes of this invention the term "arylalkyl" is defined as aryl-$C_1$–$C_6$-alkyl-; arylalkyl moieties include benzyl, 1-phenylethyl, 2-phenylethyl, 3-phenylpropyl, 2-phenylpropyl and the like. For purposes of this invention the term "cycloalkylalkyl" denotes an alkyl group as defined above that is further substituted with a cycloalkyl group as defined above.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor—containing highly active antiretroviral therapy (HAART) for the treatment of diseases which originate from fibrinolytic impairment and hyper-coagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type I and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

Methods for the treatment, inhibition, prevention or prophylaxis in a mammal of each of the conditions or maladies listed herein are part of the present invention. Each method comprises administering to a mammal in need thereof a pharmaceutically or therapeutically effective amount of a compound of this invention, or a pharmaceutically acceptable salt or ester form thereof.

Each of the methods described herein comprise administering to a mammal in need of such treatment a pharmaceutically effective amount of a compound of this invention, or a pharmaceutically acceptable salt or ester form thereof. It will be understood that a pharmaceutically effective amount of the compound will be at least the minimum amount necessary to provide an improvement in the symptoms or underlying causation of the malady in question or to inhibit or lessen the onset of symptoms of the malady.

The present invention is thus further directed to a method of inhibiting plasminogen activator inhibitor (PAI-1) in a mammal comprising administering to a mammal in need thereof a therapeutically effective amount of a compound of Formula (I):

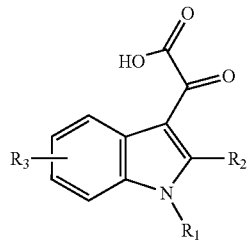

(I)

wherein:
$R_1$ is: a) the moiety:

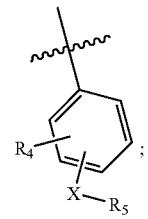

or
b) $C_1$–$C_8$ alkyl, benzo[1,3]dioxo-5yl-methyl, cycloalkylalkyl where the alkyl chain is $C_1$–$C_3$, heteroarylalkyl where the alkyl chain is $C_1$–$C_3$, arylalkyl where the alkyl chain is $C_1$–$C_3$, preferably selected from benzyl, $CH_2$-1-naphthyl, $CH_2$-2-naphthyl, $CH_2CH_2$-phenyl, or $CH_2CH_2$-naphthyl, wherein the alkyl, cycloalkyl, heteroaryl, phenyl, benzyl, and naphthyl, groups may be optionally substituted by from 1 to 3 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —$C(O)CH_3$, —$CO_2R_7$, —$C(O)NH_2$, —$S(O)_2CH_3$, —OH, —$NH_2$, or —$NO_2$;

$R_4$ is hydrogen, halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —COOH, —$CH_2CO_2H$, —$C(O)CH_3$, —$CO_2R_7$, —$C(O)NH_2$, —$S(O)_2CH_3$, —OH, —$NH_2$, or —$NO_2$;

X is O, S, or NH;

$R_5$ is $C_1$–$C_8$ alkyl, $C_1$–$C_3$ perfluoroalkyl, $C_3$–$C_6$ cycloalkyl, —$CH_2$—$C_3$–$C_6$ cycloalkyl, heteroaryl, —$CH_2$-heteroaryl, phenyl, or arylalkyl where the alkyl chain is $C_1$–$C_8$, wherein the rings of the cycloalkyl, heteroaryl, phenyl, and aryl groups may be optionally substituted by from 1 to 5 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —COOH, —$CH_2CO_2H$, —$C(O)CH_3$, —$CO_2R_7$, —$C(O)NH_2$, —$S(O)_2CH_3$, —OH, —$NH_2$, or —$NO_2$;

$R_2$ is hydrogen, $C_1$–$C_6$ alkyl, —$CH_2$—$C_3$–$C_6$ cycloalkyl, or $C_1$–$C_3$ perfluoroalkyl, wherein the alkyl and cycloalkyl groups may be optionally substituted by halogen, —CN, $C_1$–$C_6$ alkoxy, —COOH, —$CH_2CO_2H$, —$C(O)CH_3$, —$CO_2R_7$, —$C(O)NH_2$, —$S(O)_2CH_3$, —OH, —$NH_2$, or —$NO_2$;

$R_3$ is: (a) hydrogen, halogen, $C_1$–$C_8$ alkyl, $C_1$–$C_8$ alkenyl, $C_1$–$C_8$ alkynyl, $C_3$–$C_6$ cycloalkyl, —$CH_2$—$C_3$–$C_6$ cycloalkyl, heteroaryl, or phenyl, wherein the alkyl, alkenyl, alkynyl, cycloalkyl, heteroaryl, and phenyl groups may be optionally substituted by from 1 to 3 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —$OCHF_2$, —CN, —COOH, —$CH_2CO_2H$, —$C(O)CH_3$, —$CO_2R_7$, —$C(O)NH_2$, —$S(O)_2CH_3$, —OH, —$NH_2$, or —$NO_2$;

or (b) the moiety X—$R_6$;

$R_6$ is $C_1$–$C_8$ alkyl, $C_1$–$C_8$ alkenyl, $C_1$–$C_8$ alkynyl, $C_3$–$C_6$ cycloalkyl, —$CH_2$—$C_3$–$C_6$ cycloalkyl, heteroaryl, phenyl, aryl-alkyl where the alkyl chain is $C_1$–$C_8$, $CH_2CH_2$-phenyl, or $CH_2CH_2$-naphthyl, wherein the alkyl, alkenyl, alkynyl, cycloalkyl, heteroaryl, phenyl, and naphthyl groups may be optionally substituted by from 1 to 3 groups selected from halogen, $C_1$–$C_3$ alkyl, $C_1$–$C_3$ perfluoroalkyl, preferably —$CF_3$, —O—$C_1$–$C_3$ perfluoroalkyl, preferably —$OCF_3$, —S—$C_1$–$C_3$ perfluoroalkyl, preferably —$SCF_3$, $C_1$–$C_3$ alkoxy, —$OCHF_2$, —CN, —$C(O)CH_3$, —$CO_2R_7$, —$S(O)_2CH_3$, —OH, —$NH_2$, or —$NO_2$; and $R_7$ is $C_1$–$C_6$ alkyl, $C_3$–$C_6$ cycloalkyl, —$CH_2$—$C_3$–$C_6$ cycloalkyl, or aryl-alkyl where the alkyl chain is $C_1$–$C_8$; or a pharmaceutically acceptable salt or ester form thereof.

PROCESS OF THE INVENTION

Compounds of the present invention can be readily prepared according to the methods and examples described below using readily available starting materials, reagents and conventional synthetic procedures. It is also possible to make use of variants of these process steps, which in themselves are known to and well within the preparatory skill of the medicinal chemist. In the following reaction schemes, $R_1$ through $R_8$ are selected from the groups defined above.

Method A

Substituted indole is first arylated on nitrogen with aryl iodides, bromides, chlorides, and triflates having a suitable handle for further elaboration. This handle can be, but is not limited to, an ether substituent, such as methoxy or benzyloxy. Indole may be arylated on nitrogen by reaction with aryl halides, especially aryl iodides, in the presence of copper (I) or copper (II) salts and base in a solvent such as pyridine, collidine, dimethylformamide (DMF), N-methylpyrrolidinone (NMP), or DMSO at elevated temperatures of 100 to 210° C. Indole N-arylation can also be carried out with aryl iodides, bromides, chlorides, and triflates in the presence of a base, preferably NaOt-Bu or $K_3PO_4$, and bulky, electron rich phosphine ligands in combination with $Pd_2(dba)_3$ in an inert solvent such as toluene at 80 to 100° C. The ether protecting group may then be removed by any convenient means, e.g., for methyl ethers, treatment with $BBr_3$ in an inert solvent such as dichloromethane (DCM) at −78 to +25° C. or, for benzyl ethers, hydrogenation over palladium on carbon (Pd—C) in a polar solvent, such as methanol. The hydroxyl group can then in turn be alkylated with an alkyl or benzyl iodide, bromide, chloride, or triflate in the presence of a base, such as KOH or NaH, in an inert solvent, such as THF, dioxane, pyridine, DMF, NMP, or DMSO, at −40 to +100° C. The product can then be reacted with 1–100 equivalents oxalyl chloride, either neat or in an inert solvent such as DCM, THF, or dioxane, at −40 to +64° C. The resulting glyoxylic chloride intermediate can be hydrolyzed with water or with an aqueous solution of base, such as $Na_2CO_3$, $NaHCO_3$, or NaOH. The resulting solution may be acidified and extracted with a hydrophobic solvent such as dichloromethane or ethyl acetate to isolate the product.

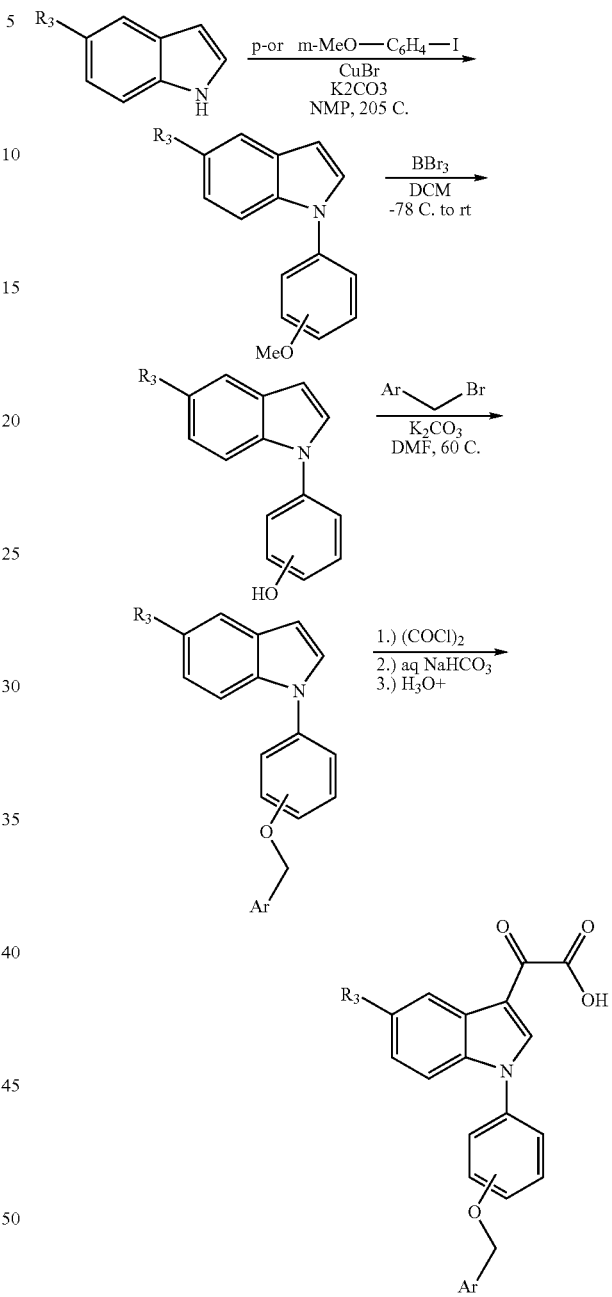

Method B 3- or 4-hydroxy indole can be alkylated in the presence of benzyl, diphenylmethyl or naphthylmethyl iodide, bromide, chloride, or triflate in the presence of a base, such as KOH or NaH, in an inert solvent, such as THF, dioxane, pyridine, DMF, NMP, or DMSO, at −40 to +100° C. The resulting ether can be selectively deprotected via hydrogenation, preferably by transfer hydrogenation, using Pd—C, a hydrogen source, such as $H_2$, $NH_4CHO$, $NH_4OAc$, $HCO_2H$, cyclohexadiene, or isopropyl alcohol, either neat or in a solvent, such as methanol, ethanol, or propanol, at 25–100° C. The resulting hyroxy indole can the be O-arylated with aryl fluoride, chloride, bromide, or iodide in the presence of a base, such as $Cs_2CO_3$ or $K_2CO_3$, in an inert solvent such as pyridine, collidine, DMF, NMP, or DMSO at 25–110° C. The ether intermediate can be converted to the glyoxylic acid product using the procedure described in Method A, above.

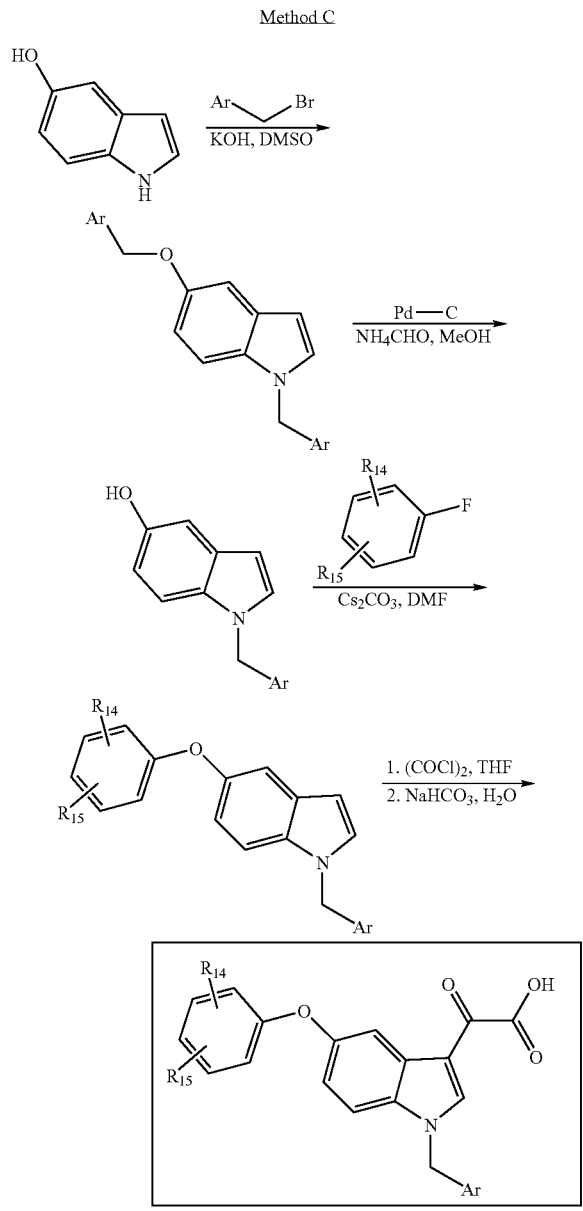

Ar = phenyl, optionally substituted phenyl, naphthyl;
$R_{14}$, $R_{15}$ = optional substitution with halogen, $C_1$–$C_3$ perfluoroalkyl, preferably —$CF_3$, $C(O)CH_3$, or —$NO_2$;

5-Hydroxyindole can be O-alkylated with aliphatic alcohols in the presence of triphenylphosphine and azodicarboxylates, especially diethyl, diisopropyl, or di-t-butyl azodicarboxylates, in an inert solvent, preferably THF, at 0–25° C. Alternately, N-benzyl-5-hydroxyindole can be prepared according to the procedure described above in Method B and alkylated in the presence of alkyl, benzyl, phenethyl, or naphthylmethyl iodide, bromide, chloride, or triflate in the presence of a base, such as $K_2CO_3$, $Cs_2CO_3$, KOH or NaH, in an inert solvent, such as THF, dioxane, pyridine, DMF, NMP, or DMSO, at −40 to +100° C. The 1H-indole intermediate can be alkylated in turn with alkyl, benzyl, phenethyl, or naphthylmethyl iodide, bromide, chloride, or triflate as just described. The resulting N,O-alkylated indole can be reacted with oxalyl chloride as described above to form the product.

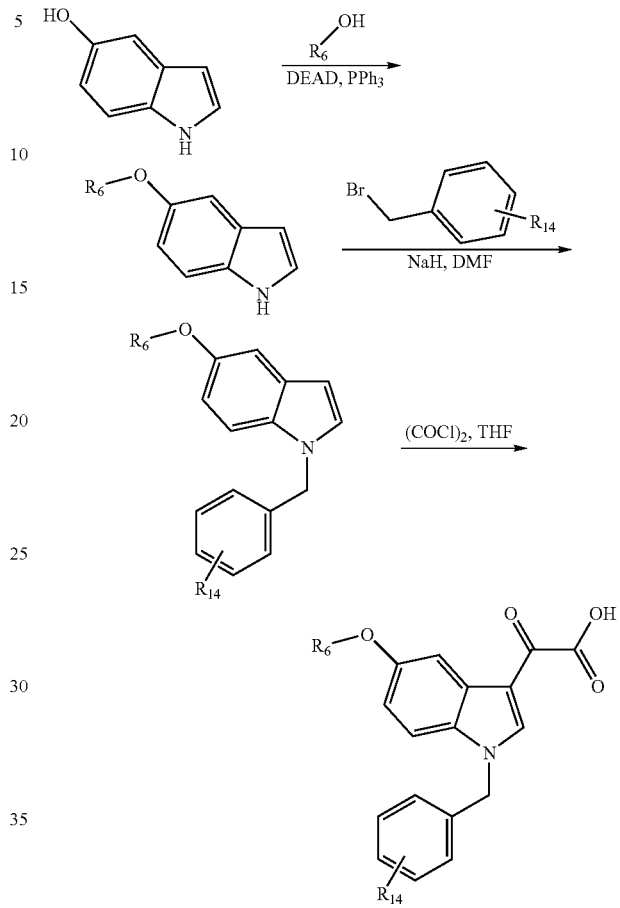

$R_{14}$ = optional substitution with halogen, $C_1$–$C_3$ perfluoroalkyl, preferably —$CF_3$, $C(O)CH_3$, or —$NO_2$;

This invention also provides pharmaceutical compositions comprising of the present invention either alone or in combination with one or more pharmaceutically acceptable carriers or excipients. Such compositions for treating conditions resulting from fibrinolytic disorder such as deep vein thrombosis and coronary heart disease, pulmonary fibrosis, etc.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physician's direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit Plasminogen Activator Inhibitor-1 was established by the following experimental procedures:

Primary Screen for the PAI-1 Inhibition

Test compounds were dissolved in DMSO at a final concentration of 10 mM, then diluted 100× in physiologic buffer. The inhibitory assay was initiated by the addition of the test compound (1–100 µM final concentration, maximum DMSO concentration of 0.2%) in a pH 6.6 buffer containing 140 nM recombinant human plasminogen activator inhibitor-1 (Molecular Innovations, Royal Oak, Mich.). Following a 1 hour incubation at room temperature, 70 nM of recombinant human tissue plasminogen activator (tPA) was added, and the combination of the test compound, PAI-1 and tPA was incubated for an additional 30 minutes. Following the second incubation, Spectrozyme-tPA (American Diagnostica, Greenwich, Conn.), a chromogenic substrate for tPA, was added and absorbance read at 405 nm at 0 and 60 minutes. Relative PAI-1 inhibition was equal to the residual tPA activity in the presence of the test compound and PAI-1. Control treatments included the complete inhibition of tPA by PAI-1 at the molar ratio employed (2:1), and the absence of any effect of the test compound on tPA alone.

Assay for Determining $IC_{50}$ of Inhibition of PAI-1

This assay was based upon the non-SDS dissociable interaction between tPA and active PAI-1. Assay plates were initially coated with human tPA (10 µg/ml). The test compounds were dissolved in DMSO at 10 mM, then diluted with physiologic buffer (pH 7.5) to a final concentration of 1–50 µM. The test compounds were incubated with human PAI-1 (50 ng/ml) for 15 minutes at room temperature. The tPA-coated plate was washed with a solution of 0.05% Tween 20 and 0.1% BSA, then the plate is blocked with a solution of 3% BSA. An aliquot of the test compound/PAI-1 solution was then added to the tPA-coated plate, incubated at room temperature for 1 hour, and washed. Active PAI-1 bound to the plate was assessed by adding an aliquot of a 1:1000 dilution of the 33B8 monoclonal antibody against human PAI-1, and incubating the plate at room temperature for 1 hour (Molecular Innovations, Royal Oak, Mich.). The plate was again washed, and a solution of goat anti-mouse IgG-alkaline phosphatase conjugate is added at a 1:50,000 dilution in goat serum. The plate was incubated 30 minutes at room temperature, washed, and a solution of alkaline phosphatase substrate was added. The plate was incubated 45 minutes at room temperature, and color development was determined at $OD_{405nm}$. The quantitation of active PAI-1 bound to tPA at varying concentrations of the test compound was used to determine the $IC_{50}$. Results were analyzed using a logarithmic best-fit equation. The assay sensitivity was 5 ng/ml of human PAI-1 as determined from a standard curve ranging from 0–100 ng/ml.

The compounds of the present invention inhibited Plasminogen Activator Inhibitor-1 as summarized in Table I.

TABLE 1

| Example | Inhibition @25 uM (%) | $IC_{50}$ (uM) |
|---|---|---|
| 1 | 23 | — |
| 2 | 43 | — |
| 3 | 78 | >25 |
| 4 | 40 (100 uM) | — |
| 5 | 26 | — |
| 6 | 54 | >25 |
| 7 | 62 | — |
| 8 | 34 (100 uM) | — |
| 9 | 44 | — |
| 10 | 1 | — |
| 11 | 66 | — |
| 12 | 32 (100 uM) | — |
| 13 | 39 | — |
| 14 | 43 | — |
| 15 | 5 | — |
| 16 | 75 | >25 |
| 17 | 49 (100 uM) | — |
| 18 | 45 | — |

TABLE 1-continued

| Example | Inhibition @25 uM (%) | IC$_{50}$ (uM) |
|---|---|---|
| 19 | 46 | — |
| 20 | 56 | >25 |
| 21 | 6 | — |
| 22 | 13 | — |
| 23 | 52 | 12.32 |
| 24 | 13 (100 uM) | — |
| 25 | 8 (100 uM) | — |
| 26 | 8 (100 uM) | — |
| 27 | 16 (100 uM) | — |
| 28 | 12 | — |
| 29 | 29 (100 uM) | — |
| 30 | 29 | — |

EXAMPLE 1

(1-{4-[(4-Cyanobenzyl)oxy]phenyl}-1H-indol-3-yl)(oxo)acetic acid

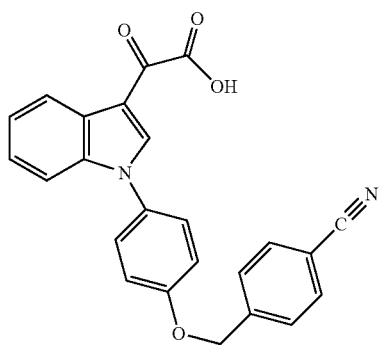

Step 1

A slurry of 2.63 g (22.5 mmol) indole, 5.26 g (22.5 mmol) 4-iodoanisole, 0.43 g (3 mmol) CuBr and 4.14 g (30 mmol) K$_2$CO$_3$ in 60 ml anhydrous N-methylpyrrolidinone (NMP) was heated to reflux with stirring for 16 hr. The solution was allowed to cool and then poured into water and shaken with ethyl acetate. The entire biphasic system was filtered through a pad of Celite, the phases were separated, and the organic phase was dried over MgSO$_4$ and concentrated. The crude product was chromatographed on silica (5–7% EtOAc-Hexane) to afford 3.53 g 1-(4-methoxyphenyl)-1H-indole as a colorless solid.

Step 2

To 2.90 g (13 mmol) 1-(4-methoxyphenyl)-1H-indole in 80 ml anhydrous DCM at −78° C. was added 2.27 ml (24 mmol) BBr$_3$. The solution was allowed to gradually warm to room temperature overnight. The solution was poured into a slurry of ice and water. Brine was added and the product was extracted with ethyl acetate. The organic phase was dried over MgSO$_4$ and concentrated. The crude product was chromatographed on SiO$_2$ to afford 0.73 g 1-(4-hydroxyphenyl)-1H-indole as an oil.

Step 3

To a solution of 0.038 g (0.18 mmol) 1-(4-hydroxyphenyl)-1H-indole in 1.2 ml DMF was added 0.05 g (0.38 mmol) K$_2$CO$_3$ and the slurry was mixed for 30 min. 59 mg (0.3 mmol) α-bromo-p-tolunitrile and 0.01 g (66 μmol) NaI was added and the slurry was mixed at 60° C. for 4 hr. The solution was allowed to cool and an additional 2 ml DMF was added, followed by 0.10 g PS-Trisamine scavenger reagent (Argonaut Technologies, San Carlos, Calif.). The slurry was mixed at 60° C. for a further 3 hr and allowed to cool. The reaction was filtered and the solution was concentrated to afford 0.045 g 1-{4-[(4-cyanobenzyl)oxy]phenyl}-1H-indole as an oil.

Step 4

To a solution of the product from Part 3 in 1 ml THF was added 200 μl of 1M (COCl)$_2$ in THF. The solution was mixed 5 min upon which time an additional 200 μl 1M (COCl)$_2$ was added. The solution was heated to 55° C. for 6 hr and allowed to cool. The solution was drained from the reaction vessel into a vial containing 2 ml aqueous NaHCO$_3$ and the biphasic system was mixed overnight whereupon 1 ml 2N aqueous HCl was added. The product was extracted with 2 ml DCM, the organic phase separated and concentrated. The residue was purified by RP-HPLC (See Note 1 below) to give (1-{4-[(4-cyanobenzyl)oxy]phenyl}-1H-indol-3-yl)(oxo)acetic acid (19.9 mg) as an oil. LC/MS Data (See Note 2 below) (molecular ion and retention time): m/z 397 (M+H); 1.97 min.

Note 1. Semi-preparative RP-HPLC Conditions:
  Gilson Semi-Preparative HPLC system with Unipoint Software
  Column: Phenomenex C$_{18}$ Luna 21.6 mm×60 mm, 5 μM;
  Solvent A: Water (0.02% TFA buffer); Solvent B: Acetonitrile (0.02% TFA buffer); Solvent Gradient: Time 0: 5% B; 2.5 min: 5% B; 7 min: 95% B; Hold 95% B 5 min.
  Flow Rate: 22.5 mL/min
  The product peak was collected based on UV absorption and concentrated.

Note 2. Analytical LC/MS Conditions:
  Hewlett Packard 1100 MSD with ChemStation Software
  Column: YMC ODS-AM 2.0 mm×50 mm 5μ column at 23° C.
  Solvent A: Water (0.02% TFA buffer)
  Solvent B: Acetonitrile (0.02% TFA buffer)
  Gradient: Time 0: 5% B; 0.3 min: 5% B; 3.0 min: 90% B; Hold 95% B 2 min.
  Flow rate 1.5 mL/min
  Detection: 254 nm DAD; API-ES Scanning Mode Positive 150–700; Fragmentor 70 mV.

The compounds of Examples 2–19 were prepared by the same steps as set forth in Example 1 using indole, 5-fluoroindole, 5-methylindole, 5-chloroindole, 4-iodoanisole, 3-iodoanisole, α-bromo-p-tolunitrile, 3-methoxybenzylbromide, 3-chlorobenzylbromide, 3,5-dimethoxybenzylbromide, 4-t-butylbenzylbromide, 2,4-dichlorobenzylbromide, 2,3,5,6-tetrafluoro-4-(trifluoromethyl)benzyl bromide, 4-(4-bromomethyl)phenyl-1,2,3-thiadiazole, 4-(bromomethyl)-2,6-dichloropyridine, and ethyl 5-chloromethylfuran carboxylate.

| Example | Chemical Name | m/z, Retention Time (min) |
|---|---|---|
| 2 | {1-[4-(3-Methoxybenzyloxy)phenyl]-1H-indol-3-yl}(oxo)acetic acid | 402 (M + H); 2.25 min |
| 3 | {1-[4-(3-Chlorobenzyloxy)phenyl]-1H-indol-3-yl}(oxo)acetic acid | 402 (M + H); 2.25 min |

-continued

| Example | Chemical Name | m/z, Retention Time (min) |
|---|---|---|
| 4 | {1-[4-(4-Cyanobenzyloxy)phenyl]-5-fluoro-1H-indol-3-yl}(oxo)acetic acid | |
| 5 | {1-[4-(3,5-Dimethoxybenzyloxy) phenyl]-5-fluoro-1H-indol-3-yl}(oxo)acetic acid | 450 (M + H); 2.30 min |
| 6 | {1-[4-(3-Chlorobenzyloxy)phenyl]-5-methyl-1H-indol-3-yl}(oxo)acetic acid | 420 (M + H); 2.90 min[3] |
| 7 | {1-[4-(4-tert-Butylbenzyloxy) phenyl]-5-methyl-1H-indol-3-yl}(oxo)acetic acid | 442 (M + H); 3.45 min |
| 8 | {1-[4-(2,4-Dichlorobenzyloxy) phenyl]-5-methyl-1H-indol-3-yl}(oxo)acetic acid | |
| 9 | {5-Chloro-1-[3-(4-cyanobenzyloxy) phenyl]-1H-indol-3-yl}(oxo)acetic acid | 431 (M + H); 2.35 min |
| 10 | {5-Chloro-1-[3-(3,5-dimethoxy benzyloxy)phenyl]-1H-indol-3-yl}(oxo)acetic acid | |
| 11 | {1-[4-(2,3,5,6-tetrafluoro-4-trifluoromethylbenzyloxy)phenyl]1H-indol-3-yl}(oxo)acetic acid | 512 (M + H); 2.88 min |
| 12 | {1-[4-(4-[1,2,3]thiadiazol-4-ylbenzyloxy)phenyl]-1H-indol-3-yl}(oxo)acetic acid | |
| 13 | {1-[4-(2,6-Dichloropyridin-4-ylmethoxy)phenyl]1H-indol-3-yl}(oxo)acetic acid | 441 (M + H); 2.42 min |
| 14 | 5-[4-(5-Fluoro-3-carboxy(oxo) methyl-1H-indol-1-yl)phenoxy methyl]furan-2-carboxylic acid ethyl ester | 452 (M + H); 1.97 min |
| 15 | {1-[4-(2,6-dichloropyridin-4-ylmethoxy)phenyl]-5-methyl-1H-indol-3-yl}(oxo)acetic acid | |
| 16 | {5-Chloro-1-[3-(2,3,5,6-tetrafluoro-4-trifluoromethylbenzyloxy) phenyl]1H-indol-3-yl}(oxo)acetic acid | |
| 17 | 5-[3-(5-Chloro-3-carboxy(oxo) methyl-1H-indol-1-yl)phenoxy methyl]furan-2-carboxylic acid ethyl ester | |
| 18 | {5-Chloro-1-[3-(4-[1,2,3]thiadiazol-4-ylbenzyloxy)phenyl]-1H-indol-3-yl}(oxo)acetic acid | 490 (M + H); 2.57 min |
| 19 | {5-Chloro-1-[3-(2,6-dichloropyridin-4-ylmethoxy)phenyl]-1H-indol-3-yl}(oxo)acetic acid | 475, 477 (M + H); 2.80 min |

Note 3. Example 5 was resynthesized on a larger scale by a different route and recrystalized from EtOAc to give a yellow solid: m.p. 175–177° C.; $^1$H NMR (CDCl$_3$, 400 MHz) δ 2.49 (s, 3H), 5.23 (s, 2H), 7.17 (d, J=8 Hz, 1H), 7.25 (d, J=8 Hz, 2H), 7.34 (d, J=8 Hz, 1H), 7.40–7.50 (m, 3H), 7.57–7.63 (m, 4H), 8.10 (s, 1H), 8.47 (s, 1H); MS: m/z (ESI) 420 (M+H); Anal. calcd for (C$_{24}$H$_{18}$ClNO$_4$) C, H, N.

EXAMPLE 20

[1,5-Bis-(4-trifluoromethoxy-phenyl)-1H-indol-3-yl]-oxo-acetic acid

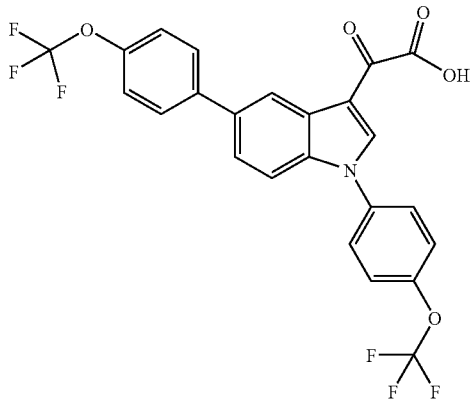

Step 1

A stirred slurry of 6.56 g (62 mmol) Na$_2$CO$_3$, 3.03 g (15.5 mmol) 5-bromoindole, 3.415 g (16.5 mmol) 4-(trifluoromethoxy)phenylboronic acid, and 0.50 g (0.43 mmol) tetrakistriphenylphosphine palladium was heated to reflux for 3 hr. The reaction mixture was allowed to cool and was then poured into 300 mL water and shaken with ethyl acetate. The combined aqueous and organic phases were filtered and the organic layer was separated, dried over MgSO$_4$, and concentrated. The residue was chromatographed on silica (eluting with 20–33% EtOAc-hexane) to afford 2.49 g (58%) 5-[4-(trifluoromethoxy)phenyl]indole as a solid.

Step 2

A mixture of 0.6 g (2.6 mmol) 5-(4-trifluoromethoxyphenyl)-1H-indole, 0.53 mL (2.8 mmol) 4-(trifluoromethoxy)iodobenzene, 0.075 g (0.52 mmol) copper(I) bromide and 0.54 g (3.9 mmol) K$_2$CO$_3$ in 10 mL anhydrous N-methylpyrrolidinone was heated to reflux overnight with stirring. The reaction was allowed to cool and was then poured into 200 mL of water. The aqueous solution was shaken with 200 mL ethyl acetate, the combined aqueous and organic phases were filtered, and the organic phase was separated. The aqueous phase was extracted once more with 200 mL ethyl acetate and the combined organic phases were washed with brine and concentrated. The crude product was chromatographed on silica (5–7% EtOAc-hexane as elutant) to afford 0.505 g (44% yield) of 1,5-bis-(4-trifluoromethoxy-phenyl)-1H-indole.

Step 3 of Example 14 was conducted using the Quest 210 Parallel Synthesizer (Argonaut Technologies, San Carlos, Calif.) using 5 mL Teflon reaction vessels. Mixing of the reaction mixtures was achieved by the vertical motion of a magnetic stir bar within the reaction vessel. Drainage of the reaction vessels was accomplished by the application of a positive pressure of nitrogen to the reaction vessel.

Step 3

To a solution of 0.505 g (1.15 mmol) 1,5-bis-(4-trifluoromethoxy-phenyl)-1H-indole in 3 mL anhydrous THF was added 0.13 mL (2.9 mmol) oxalyl chloride. The solution was mixed at room temperature for 18 hr, upon which time the contents of the reaction vessel were drained into a vial containing 10 mL aqueous NaHCO$_3$. The vial was capped and shaken and then the solution was acidified by the dropwise addition of 10 mL 2N aqueous HCl. The organic phase was removed and concentrated. The crude product was purified by RP-HPLC (See Note 1) to afford 0.142 g [1,5-bis-(4-trifluoromethoxy-phenyl)-1H-indol-3-yl]-oxo-acetic acid ethyl ester.

Step 4

To a solution of 0.142 g [1,5-bis-(4-trifluoromethoxy-phenyl)-1H-indol-3-yl]-oxo-acetic acid ethyl ester from Step 3 in 1 mL THF was added 2 ml 0.5M aqueous LiOH. The reaction was mixed using orbital shaking for 5 hr, at which time TLC indicated that the reaction was complete. The solution was acidified by the dropwise addition of 2N aqueous HCl and extracted with dichloromethane. The organic phase was dried by filtration through a ChemElute column (Varian Inc., Palo Alto, Calif.) and the solvent was evaporated to afford 82 mg [1,5-Bis-(4-trifluoromethoxy-phenyl)-1H-indol-3-yl]-oxo-acetic acid as a yellow solid: $^1$H NMR (CDCl$_3$, 400 MHz) δ 9.13 (s, 1H), 8.64 (s, 1H), 7.70 (d, J=6.6 Hz, 2H), 7.57–7.68 (m, 3H), 7.46–7.56 (m, 3H), 7.33 (d, J=8 Hz, 2H), MS: m/z (ESI) 508.2 (M−H);

EXAMPLE 21

{1-(4-fluorobenzyl)-5-[2-(4-fluorophenyl)ethoxy]-1H-indol-3-yl}(oxo)acetic acid

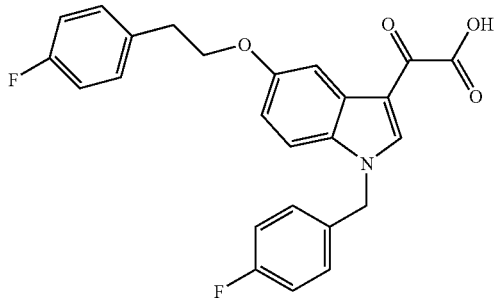

Step 1

To a solution of 1.06 g (8 mmol) 5-hydroxyindole and 2.09 g (8 mmol) triphenylphosphine in 40 ml anhydrous THF, cooled to 0° C. in ice, was added 1.0 mL (8 mmol) 4-fluorophenethylalcohol and 1.6 ml (8 mmol) diisopropylazodicarboxylate. The solution was allowed to gradually come to room temperature overnight. The solution was concentrated and the residue was chromatographed on silica using 20–25% EtOAc-hexane to afford 0.525 g 5-[2-(4-fluoro-phenyl)-ethoxy]-1H-indole as a white solid.

Step 2

To 0.2 g of a 60% dispersion of NaH in mineral oil, suspended in 20 ml of anhydrous THF, was added 0.61 g (2.38 mmol) 5-[2-(4-fluoro-phenyl)-ethoxy]-1H-indole from Step 1. The slurry was stirred for 15 min upon which time 0.33 ml (2.6 mmol) 4-fluorobenzylbromide was added. The slurry was stirred overnight. The slurry was concentrated under vacuum and the residue was redissolved in ethyl acetate and washed with brine. The organic phase was dried over MgSO$_4$ and concentrated. The residue was chromatographed on silica to afford 0.61 g 1-(4-fluoro-benzyl)-5-[2-(4-fluoro-phenyl)-ethoxy]-1H-indole as a fluffy powder.

Step 3

To a solution of the product from Part 3 in 10 ml anhydrous THF was added 0.30 ml of (COCl)$_2$. The solution was stirred at room temperature over 4 nights. The solution was poured into a flask containing 20 ml aqueous NaHCO$_3$. 10 ml 2N aqueous HCl was added to acidify, the solution was extracted with DCM, and the organic phase was concentrated. The residue was purified by RP-HPLC (See Note 1 above) to give 0.43 g as yellow crystals: m.p. 171–173° C.; $^1$H NMR (CDCl$_3$, 400 MHz) δ 3.10 (t, J=6.8 Hz, 2H), 4.24 (t, J=6.8 Hz, 2H), 5.33 (s, 2H), 6.90–6.93 (m, 1H), 6.97–7.05 (m, 4H), 7.14–7.18 (m, 3H), 7.24–7.28 (m, 2H), 7.85 (s, 1H), 8.92 (s, 1H); MS: m/z (ESI) 434 (M−H).

EXAMPLE 22

(1-Benzyl-5-benzyloxy-1H-indol-3-yl)-oxo-acetic acid

Using 1-benzyl-5-benzyloxy-1H-indole, (1-benzyl-5-benzyloxy-1H-indol-3-yl)-oxo-acetic acid was prepared following the procedure of Step 3 of Example 21: $^1$H NMR (CDCl$_3$, 400 MHz) δ 8.60 (s, 1H), 7.79 (d, J=2.5 Hz, 1H), 7.45–7.52 (m, 3H), 7.25–7.43 (m, 7H), 6.99 (dd, J=6.8, 2.5 Hz, 1H), 5.55 (s, 2H), 5.13 (s, 2H), MS: m/z (ESI) 386 (M+H).

EXAMPLE 23

[1-Benzyl-5-(2-chloro-4-trifluoromethyl-phenoxy)-1H-indol-3-yl](oxo)acetic acid

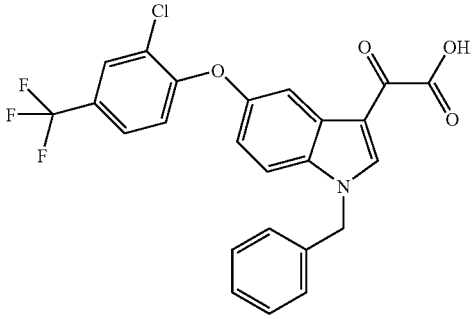

A slurry of 0.98 g (3.12 mmol) 1-benzyl-5-benzyloxy-1H-indole, 0.20 g 20% Palladium on carbon, and 1.51 g (24 mmol) NH$_4$CHO was heated to reflux with stirring for 3 days. The reaction was allowed to cool and an additional 0.20 g 20% Palladium on carbon and 1.33 g NH$_4$CHO was added. The reaction was refluxed for an additional 24 hours upon which time the reaction was complete by TLC. The reaction was filtered through paper and concentrated. The residue was chromatographed on silica using 25–40% EtOAc-hexane to afford 0.44 g 1-benzyl-5-hydroxy-1H-indole as a solid.

Step 2

A slurry of 0.413 g (1.85 mmol) 1-benzyl-5-hydroxy-1H-indole, 0.3 ml (2.2 mmol) 3-chloro-4-fluorobenzotrifluoride, and 1.0 g (3.0 mmol) Cs$_2$CO$_3$ in 12 ml DMF was heated to 130° C. with stirring for 16 hr. The solution was allowed to cool and then filtered to remove Cs$_2$CO$_3$. The solution was concentrated under vacuum and chromatographed on silica using 5–7% EtOAc-hexane to afford 0.51 g 1-benzyl-5-(2-chloro-4-trifluoromethyl-phenoxy)-1H-indole as an oil.

Step 3

To a solution of the product from Part 2 in 8 ml anhydrous THF was added 0.22 ml of (COCl)$_2$. The solution was stirred at room temperature for 4 hr. 10 ml saturated aqueous NaHCO$_3$ was added and the biphasic system was stirred for ½ hr. 2N aqueous HCl was added to acidify, the solution was extracted with DCM, and the organic phase was concentrated. The residue was purified by RP-HPLC[1] to give 0.315 g as yellow crystals: m.p. 152–154° C.; $^1$H NMR (CDCl$_3$, 400 MHz) δ 5.42 (s, 2H), 6.89 (d, J=4.4 Hz, 1H), 7.05 (dd, J=6.2 Hz, 1.2 Hz, 1H), 7.20–7.25 (m, 2H), 7.34–7.40 (m, 5H), 7.74 (s, 1H), 8.06 (s, 1H), 9.04 (s, 1H); MS: m/z (ESI) 472 (M–H).

EXAMPLE 24

(5-Allyloxy-1-cyclobutylmethyl-1H-indol-3-yl)-oxo-acetic acid

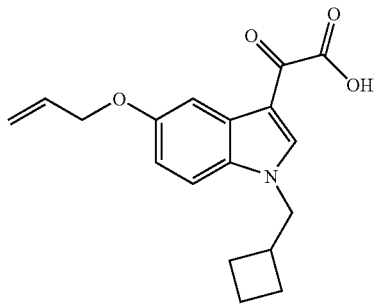

To a slurry of 2.92 g (22 mmol) 5-hydroxyindole and 12.43 g (90 mmol) K$_2$CO$_3$ in 110 mL acetone was added 2.07 mL (24 mmol) allyl bromide. The reaction was stirred at room temperature over 2 days upon which time TLC indicated that the reaction was not complete. Additional 0.66 mL allyl bromide was added and the reaction was heated to reflux for 1.5 hr and stirred at room temperature over night. The reaction was filtered to remove precipitate and concentrated. The crude product was chromatographed on silica gel using 20–33% EtOAc-hexane to afford 3.128 g (18 mmol) 5-allyloxyindole as an oil.

Step 2

To a slurry of 0.45 g (9.4 mmol) sodium hydride (50% dispersion in mineral oil) in 40 mL anhydrous THF was added 1.90 g 5-allyloxyindole. The slurry was stirred at room temperature for 15 min upon which time 1.14 mL (9 mmol) benzene sulfonyl chloride was added dropwise. The reaction was stirred at room temperature over three nights and then poured into water and extracted with ethyl acetate. The organic extracts were dried over MgSO$_4$ and concentrated. The product solidified upon concentration and the crude material was triturated with diethyl ether to afford 1.36 g of 5-allyloxy-1-benzenesulfonyl-1H-indole as a light brown solid.

Step 3

To a solution of 43 mg (0.14 mmol) 5-allyloxy-1-benzenesulfonyl-1H-indole in 1.6 mL toluene in a screw-cap vial was added 31 μL (0.4 mmol) cyclobutanemethanol and 0.66 mL 0.6M solution of sodium bis(trimethylsilylamide) in toluene. The solution was heated to 100° C. overnight with orbital shaking. The reaction was concentrated and the crude product was redissolved in 2.4 mL 1N aqueous HCl and the aqueous solution was extracted with 1.6 mL dichloromethane. The phases were separated and the organic phase was concentrated and the residue was dried under vacuum with moderate heating (approximately 50° C.) overnight.

Step 4

The crude 5-allyloxy-1-cyclobutylmethyl-1H-indole from Step 3 was dissolved in 0.5 mL anhydrous THF and 0.22 mL (2.5 mmol) oxalyl chloride was added. The reaction was mixed overnight on an orbital shaker. The reaction was concentrated and the crude product was redissolved in a minimum volume of dichloromethane. 0.8 mL 1N aqueous NaOH was added and the reaction was capped and shaken. The solution was acidified by the dropwise addition of 2N aqueous HCl and extracted with 1.6 mL dichloromethane. LC/MS (see Note 2) indicated that the reaction was not complete. The crude material was redissolved in 0.5 mL anhydrous THF, 0.16 mL oxalyl chloride was added, and the reaction was mixed at 40° C. for 6 hr with orbital shaking. The reaction was worked up as described previously and the crude products were purified by RP-HPLC (see Note 1) to afford 6.2 mg (19.8 μmol) (5-allyloxy-1-cyclobutylmethyl-1H-indol-3-yl)-oxo-acetic acid: LC/MS Data (molecular ion and retention time): m/z 312 (M–H); 2.49 min.

Using the procedures set forth in Steps 3 and 4 of Example 24 and using phenethylalcohol, piperonyl alcohol, 4-methoxyphenethyl alcohol, 1-napthyleneethanol, 3-trifluoromethylphenethyl alcohol, and 4-bromophenethyl alcohol, compounds of Examples 25–30 were prepared.

| Example | Chemical Name | m/z, Retention Time |
|---|---|---|
| 25 | (5-Allyloxy-1-phenethyl-1H-indol-3-yl)-oxo-acetic acid | 348 (M − H); 2.62 min |
| 26 | (5-Allyloxy-1-benzo[1,3]dioxol-5-ylmethyl-1H-indol-3-yl)-oxo-acetic acid | 378 (M − H); 2.64 min |
| 27 | {5-Allyloxy-1-[2-(4-methoxyphenyl)-ethyl]-1H-indol-3-yl}-oxo-acetic acid | 378 (M − H); 2.57 min |
| 28 | [5-Allyloxy-1-(2-naphthalen-1-yl-ethyl)-1H-indol-3-yl]-oxo-acetic acid | 398 (M − H); 2.84 min |
| 29 | {5-Allyloxy-1-[2-(3-trifluoromethylphenyl)-ethyl]-1H-indol-3-yl}-oxo-acetic acid | 416 (M + H); 2.82 min |
| 30 | {5-Allyloxy-1-[2-(4-bromophenyl)-ethyl]-1H-indol-3-yl}-oxo-acetic acid | 428 (M + H); 2.79 min |

What is claimed:

1. A compound of formula I:

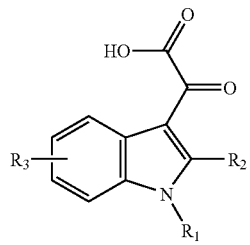

(I)

wherein:

R$_1$ is the moiety:

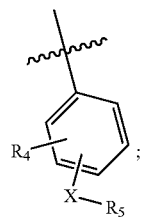

R$_4$ is hydrogen, halogen, C$_1$–C$_3$ alkyl, C$_1$–C$_3$ haloalkyl, C$_1$–C$_3$ perfluoroalkyl, C$_1$–C$_3$ alkoxy, C$_1$–C$_3$ perfluoroalkoxy, $C_1$–$C_3$ alkylthio, $C_1$–$C_3$ perfluoroalkylthio, —OCHF$_2$, —CN, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;

X is O;

$R_5$ is $C_1$–$C_8$ alkyl, $C_1$–$C_3$ perfluoroalkyl, $C_3$–$C_6$ cycloalkyl, —CH$_2$—$C_3$–$C_6$ cycloalkyl, heteroaryl, —CH$_2$-heteroaryl, phenyl, or arylalkyl where the alkyl chain is $C_1$–$C_8$, wherein the rings of the cycloalkyl, heteroaryl, phenyl, and aryl groups are optionally substituted by from 1 to 5 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —OCHF$_2$, —CN, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;

$R_2$ is hydrogen, $C_1$–$C_6$ alkyl, —CH$_2$—$C_3$–$C_6$ cycloalkyl, or $C_1$–$C_3$ perfluoroalkyl, wherein the alkyl and cycloalkyl groups are optionally substituted by halogen, —CN, $C_1$–$C_6$ alkoxy, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;

$R_3$ is: (a) hydrogen, halogen, $C_1$–$C_8$ alkyl, $C_1$–$C_8$ alkenyl, $C_1$–$C_8$ alkynyl, $C_3$–$C_6$ cycloalkyl, —CH$_2$—$C_3$–$C_6$ cycloalkyl, heteroaryl, or phenyl, wherein the alkyl, alkenyl, alkynyl, cycloalkyl, heteroaryl, and phenyl groups are optionally substituted by from 1 to 3 groups selected from halogen, $C_1$–$C_3$ alkyl, $C_1$–$C_3$ haloalkyl, $C_1$–$C_3$ perfluoroalkyl, $C_1$–$C_3$ alkoxy, $C_1$–$C_3$ perfluoroalkoxy, $C_1$–$C_3$ alkylthio, $C_1$–$C_3$ perfluoroalkylthio, —OCHF$_2$, —CN, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;

or (b) the moiety X—$R_6$;

$R_6$ is $C_1$–$C_8$ alkyl, $C_1$–$C_8$ alkenyl, $C_1$–$C_8$ alkynyl, $C_3$–$C_6$ cycloalkyl, —CH$_2$—$C_3$–$C_6$ cycloalkyl, heteroaryl, phenyl, aryl-alkyl where the alkyl chain is $C_1$–$C_8$, CH$_2$CH$_2$-phenyl, or CH$_2$CH$_2$-napthyl, wherein the alkyl, alkenyl, alkynyl, cycloalkyl, heteroaryl, phenyl, and napthyl groups are optionally substituted by from 1 to 3 groups selected from halogen, $C_1$–$C_3$ alkyl, $C_1$–$C_3$ perfluoroalkyl, —O—$C_1$–$C_3$ perfluoroalkyl, —S—$C_1$–$C_3$ perfluoroalkyl, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$; and $R_7$ is $C_1$–$C_6$ alkyl, $C_3$–$C_6$ cycloalkyl, —CH$_2$—$C_3$–$C_6$ cycloalkyl, or aryl-alkyl where the alkyl chain is $C_1$–$C_8$;

or a pharmaceutically acceptable salt or ester form thereof.

2. A compound of formula (II):

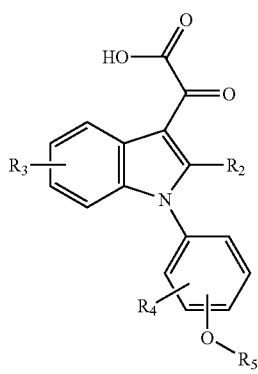

(II)

wherein:

$R_4$ is hydrogen, halogen, $C_1$–$C_6$ alkyl, $C_1$–$C_3$ haloalkyl, $C_1$–$C_3$ perfluoroalkyl, —O—$C_1$–$C_3$ perfluoroalkyl, —S—$C_1$–$C_3$ perfluoroalkyl, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$;

$R_5$ is $C_1$–$C_8$ alkyl, $C_1$–$C_3$ perfluoroalkyl, —CH$_2$—$C_3$–$C_6$ cycloalkyl, —CH$_2$-heteroaryl, or aryl-alkyl where the alkyl chain is $C_1$–$C_8$, wherein the rings of the cycloalkyl, heteroaryl, and aryl groups are optionally substituted by from 1 to 5 groups selected from halogen, $C_1$–$C_3$ alkyl, $C_1$–$C_3$ perfluoroalkyl, —O—$C_1$–$C_3$ perfluoroalkyl, —S—$C_1$–$C_3$ perfluoroalkyl, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$;

$R_2$ is hydrogen, $C_1$–$C_6$ alkyl, or $C_1$–$C_3$ perfluoroalkyl, wherein the alkyl group is optionally substituted by halogen, —CN, $C_1$–$C_6$ alkoxy, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;

$R_3$ is hydrogen, halogen, $C_1$–$C_8$ alkyl, $C_1$–$C_8$ alkenyl, $C_1$–$C_8$ alkynyl, $C_3$–$C_6$ cycloalkyl, —CH$_2$—$C_3$–$C_6$ cycloalkyl, heteroaryl, or phenyl, wherein the alkyl, alkenyl, alkynyl, cycloalkyl, heteroaryl, and phenyl groups are optionally substituted by from 1 to 3 groups selected from halogen, $C_1$–$C_3$ alkyl, $C_1$–$C_3$ perfluoroalkyl, —S—$C_1$–$C_3$ perfluoroalkyl, —S—$C_1$–$C_3$ perfluoroalkyl, $C_1$–$C_3$ alkoxy, —OCHF$_2$, —CN, —C(O)CH$_3$, —CO$_2$R$_7$, —S(O)$_2$CH$_3$, —OH, —NH$_2$, or —NO$_2$;

$R_7$ is $C_1$–$C_6$ alkyl, $C_3$–$C_6$ cycloalkyl, —CH$_2$—$C_3$–$C_6$ cycloalkyl, or aryl-alkyl where the alkyl chain is $C_1$–$C_8$;

or a pharmaceutically acceptable salt or ester form thereof.

3. The compound of claim 1 which is (1-{4-[(4-cyanobenzyl)oxy]phenyl}-1H-indol-3-yl)(oxo)acetic acid, or a pharmaceutically acceptable salt or ester form thereof.

4. The compound of claim 1 which is {1-[4-(3-methoxybenzyloxy)-phenyl]1H-indol-3-yl}-oxo-acetic acid, or a pharmaceutically acceptable salt or ester form thereof.

5. The compound of claim 1 which is {1-[4-(3-chlorobenzyloxy)-phenyl]1H-indol-3-yl}-oxo-acetic acid, or a pharmaceutically acceptable salt or ester form thereof.

6. The compound of claim 1 which is {1-[4-(4-cyanobenzyloxy)-phenyl]-5-fluoro-1H-indol-3-yl}-oxo-acetic acid, or a pharmaceutically acceptable salt or ester form thereof.

7. The compound of claim 1 which is {1-[4-(3,5-dimethoxy-benzyloxy)-phenyl]-5-fluoro-1H-indol-3-yl}-oxo-acetic acid, or a pharmaceutically acceptable salt or ester form thereof.

8. The compound of claim 1 which is {1-[4-(3-chlorobenzyloxy)-phenyl]-5-methyl-1H-indol-3-yl}-oxo-acetic acid, or a pharmaceutically acceptable salt or ester form thereof.

9. The compound which is {1-[4-(4-tert-butylbenzyloxy)-phenyl]-5-methyl-1H-indol-3-yl}-oxo-acetic acid, or a pharmaceutically acceptable salt or ester form thereof.

10. The compound of claim 1 which is {1-[4-(2,4-dichlorobenzyloxy)-phenyl]-5-methyl-1H-indol-3-yl}-oxo-acetic acid, or a pharmaceutically acceptable salt or ester form thereof.

11. The compound of claim 1 which is {5-Chloro-1-[3-(4-cyanobenzyloxy)-phenyl]1H-indol-3-yl}-oxo-acetic acid, or a pharmaceutically acceptable salt or ester form thereof.

12. The compound of claim 1 which is {5-Chloro-1-[3-(3,5-dimethoxy benzyloxy)-phenyl]1H-indol-3-yl}-oxo-acetic acid, or a pharmaceutically acceptable salt or ester form thereof.

13. The compound of claim 1 which is {1-[4-(2,3,5,6-tetrafluoro-4-trifluoromethyl-benzyloxy)-phenyl]1H-indol-3-yl}-oxo-acetic acid, or a pharmaceutically acceptable salt or ester form thereof.

14. The compound which is {1-[4-(4-[1,2,3]thiadiazol-4-yl-benzyloxy)-phenyl]-1H-indol-3-yl}-oxo-acetic acid, or a pharmaceutically acceptable salt or ester form thereof.

15. The compound of claim 1 which is {1-[4-(2,6-dichloro-pyridin-4-ylmethoxy)-phenyl]1H-indol-3-yl}-oxo-acetic acid, or a pharmaceutically acceptable salt or ester form thereof.

16. The compound of claim 1 which [1-(4-{[5-(ethoxycarbonyl)-2-furyl]methoxy}phenyl)-5-fluoro-1H-indol-3-yl](oxo)acetic acid, or a pharmaceutically acceptable salt or ester form thereof.

17. The compound of claim 1 which is {1-[4-(2,6-dichloropyridin-4-ylmethoxy)-phenyl]-5-methyl-1H-indol-3-yl}-oxo-acetic acid, or a pharmaceutically acceptable salt or ester form thereof.

18. The compound of claim 1 which is {5-Chloro-1-[3-(2,3,5,6-tetrafluoro-4-trifluoromethyl-benzyloxy)-phenyl]1H-indol-3-yl}-oxo-acetic acid, or a pharmaceutically acceptable salt or ester form thereof.

19. The compound of claim 1 which is [5-chloro-1-(3-{[5-(ethoxycarbonyl)-2-furyl]methoxy}phenyl)-1H-indol-3-yl](oxo)acetic acid, or a pharmaceutically acceptable salt or ester form thereof.

20. The compound which is {5-Chloro-1-[3-(4-[1,2,3]thiadiazol-4-yl-benzyloxy)-phenyl]1H-indol-3-yl}-oxo-acetic acid, or a pharmaceutically acceptable salt or ester form thereof.

21. The compound of claim 1 which is {5-Chloro-1-[3-(2,6-dichloro-pyridin-4-ylmethoxy)-phenyl]1H-indol-3-yl}-oxo-acetic acid, or a pharmaceutically acceptable salt or ester form thereof.

22. The compound of claim 1 which is [1,5-bis-(4-trifluoromethoxy-phenyl)-1H-indol-3-yl]-oxo-acetic acid, or a pharmaceutically acceptable salt or ester form thereof.

23. A pharmaceutical composition comprising a compound of claim 1 and a pharmaceutical carrier.

24. A method for the treatment of thrombosis or fibrinolytic impairment in a mammal, the method comprising administering to a mammal in need thereof a pharmaceutically effective amount of a compound of claim 1.

25. A method of claim 24 wherein the thrombosis or fibrinolytic impairment is associated with formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion.

26. A method for the treatment of peripheral arterial disease in a mammal, comprising administering to a mammal in need thereof a pharmaceutically effective amount of a compound of claim 1.

27. A method for the treatment of stroke associated with or resulting from atrial fibrillation in a mammal, comprising administering to a mammal in need thereof a pharmaceutically effective amount of a compound of claim 1.

28. A method for the treatment of deep vein thrombosis in a mammal, comprising administering to a mammal in need thereof a pharmaceutically effective amount of a compound of claim 1.

29. A method for the treatment of myocardial ischemia in a mammal, comprising administering to a mammal in need thereof a pharmaceutically effective amount of a compound of claim 1.

30. A method for the treatment of a cardiovascular disease caused by noninsulin dependent diabetes mellitus in a mammal, comprising administering to a mammal in need thereof a pharmaceutically effective amount of a compound of claim 1.

31. A method for the treatment of the formation of atherosclerotic plaques in a mammal, comprising administering to a mammal in need thereof a pharmaceutically effective amount of a compound of claim 1.

32. A method for the treatment of chronic obstructive pulmonary disease in a mammal, comprising administering to a mammal in need thereof a pharmaceutically effective amount of a compound of claim 1.

33. A method for the treatment of renal fibrosis in a mammal, comprising administering to a mammal in need thereof a pharmaceutically effective amount of a compound of claim 1.

34. A method for the treatment of polycystic oyary syndrome in a mammal, comprising administering to a mammal in need thereof a pharmaceutically effective amount of a compound of claim 1.

35. A method for the treatment of Alzheimer's disease in a mammal, comprising administering to a mammal in need thereof a pharmaceutically effective amount of a compound of claim 1.

36. A method for the treatment of breast or ovarian cancer in a mammal, comprising administering to a mammal in need thereof a pharmaceutically effective amount of a compound of claim 1.

37. A compound of claim 1 wherein:
$R_5$ is arylalkyl where the alkyl chain is $C_1$—$C_8$, wherein the aryl group is optionally substituted by from 1 to 5 groups selected from halogen, $C_1$—$C_3$ alkyl, $C_1$—$C_3$ haloalkyl, $C_1$—$C_3$ perfluoroalkyl, $C_1$—$C_3$ alkoxy, $C_1$—$C_3$ perfluoroalkoxy, $C_1$—$C_3$ alkylthio, $C_1$—$C_3$ perfluoroalkylthio, —OCHF$_2$, —CN, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;
or a pharmaceutically acceptable salt or ester form thereof.

38. compound of claim 1 wherein:
$R_5$ is $C_3$—$C_6$ cycloalkyl, —CH$_2$—$C_3$-$C_6$ cycloalkyl, heteroaryl, —CH$_2$-heteroaryl, or arylalkyl where the alkyl chain is $C_1$—$C_8$, wherein the rings of the cycloalkyl, heteroaryl, and aryl groups are optionally substituted by from 1 to 5 groups selected from halogen, $C_1$—$C_3$ alkyl, $C_1$—$C_3$ haloalkyl, $C_1$—$C_3$ perfluoroalkyl, $C_1$—$C_3$ perfluoroalkoxy, $C_1$—$C_3$ alkylthio, $C_1$—$C_3$ perfluoroalkylthio, —OCHF$_2$, —CN, —COOH, —CH$_2$CO$_2$H, —C(O)CH$_3$, —CO$_2$R$_7$, —C(O)NH$_2$, —S(O)$_2$CH$_3$, —OH, —NH$_2$, or —NO$_2$;
or a pharmaceutically acceptable salt or ester form thereof.

39. A compound of claim 2 wherein:
$R_5$ is aryl-alkyl where the alkyl chain is $C_1$—$C_8$, wherein the aryl group is optionally substituted by from 1 to 5 groups selected from halogen, $C_1$—$C_3$ alkyl, $C_1$—$C_3$ perfluroalkyl, —O—$C_1$—$C_3$ perfluoroalkyl, S—$C_1$—$C_3$ perfluoroalkyl, $C_1$—$C_3$ alkoxy, —OCHF$_2$, —CN, —C(O)CH$_3$, —CO$_2$R$_7$, —S(O)$_2$CH$_3$, —OH, —NH$_2$, or —NO$_2$;
or a pharmaceutically acceptable salt or ester form thereof.

40. A compound of claim 2 wherein:

$R_5$ is —$CH_2$—$C_3$—$C_6$ cycloalkyl, —$CH_2$-heteroaryl, or aryl-alkyl where the alkyl chain is $C_1$—$C_8$, wherein the rings of the cycloalkyl, heteroaryl, and aryl groups are optionally substituted by from 1 to 5 groups selected from halogen, $C_1$—$C_3$ alkyl, $C_1$—$C_3$ perfluoroalkyl, —O—$C_1$—$C_3$ perfluoroalkyl, S—$C_1$—$C_3$ perfluoroalkyl, $C_1$—$C_3$ alkoxy, —$OCHF_2$, —CN, —$C(O)CH_3$, —$CO_2R_7$, —$S(O)_2CH_3$, —OH, —$NH_2$, or —$NO_2$;

or a pharmaceutically acceptable salt or ester form thereof.

* * * * *